United States Patent [19]

Bidoia

[11] Patent Number: 5,203,863
[45] Date of Patent: Apr. 20, 1993

[54] INSTRUMENT FOR THE LIGATION OF HEMORRHOIDS OR THE LIKE

[76] Inventor: Gianfranco Bidoia, Via Bressanone, 3/A, 35100 Padova, Italy

[21] Appl. No.: 844,329

[22] Filed: Mar. 2, 1992

[30] Foreign Application Priority Data

Mar. 6, 1991 [IT] Italy ............................ 000047 A/91

[51] Int. Cl.⁵ ........................ A61M 1/00; A61B 19/00
[52] U.S. Cl. ........................................ 606/140; 606/1; 606/112; 606/115; 606/139; 604/902
[58] Field of Search ............................ 606/1, 110–115, 606/139–141, 142, 144, 145–148, 151, 228; 604/902

[56] References Cited

U.S. PATENT DOCUMENTS

| | | | |
|---|---|---|---|
| 823,877 | 6/1906 | Kellogg | 606/140 |
| 2,619,964 | 12/1952 | Thaete | 606/140 |
| 2,942,604 | 6/1960 | Graulee | 606/140 |
| 3,382,873 | 5/1968 | Banich et al. | 606/140 |
| 3,760,810 | 9/1973 | Van Hoorn | 606/140 |
| 3,964,484 | 6/1976 | Reynolds et al. | 604/902 |
| 4,257,419 | 3/1981 | Goltner et al. | 606/140 |

FOREIGN PATENT DOCUMENTS

2308846  8/1973  Fed. Rep. of Germany ...... 606/139

*Primary Examiner*—Stephen C. Pellegrino
*Assistant Examiner*—Glenn Dawson
*Attorney, Agent, or Firm*—Guido Modiano; Albert Josif

[57] ABSTRACT

The instrument for the ligation of hemorrhoids or the like includes a substantially cylindrical container with a coupling for the connection of an air aspiration apparatus and a grip handle for the operator. The container is suitable for internally accommodating a hemorrhoid or the like aspirated through its open end, on which a dilated ring-like elastic ligature, to be transferred so as to throttle the "neck" of the hemorrhoid or the like, is arrangeable externally and circumferentially. The instrument is characterized in that the container is provided with a thumb-actuated hole for adjusting the pressure inside it while the aspiration apparatus is operating.

6 Claims, 1 Drawing Sheet

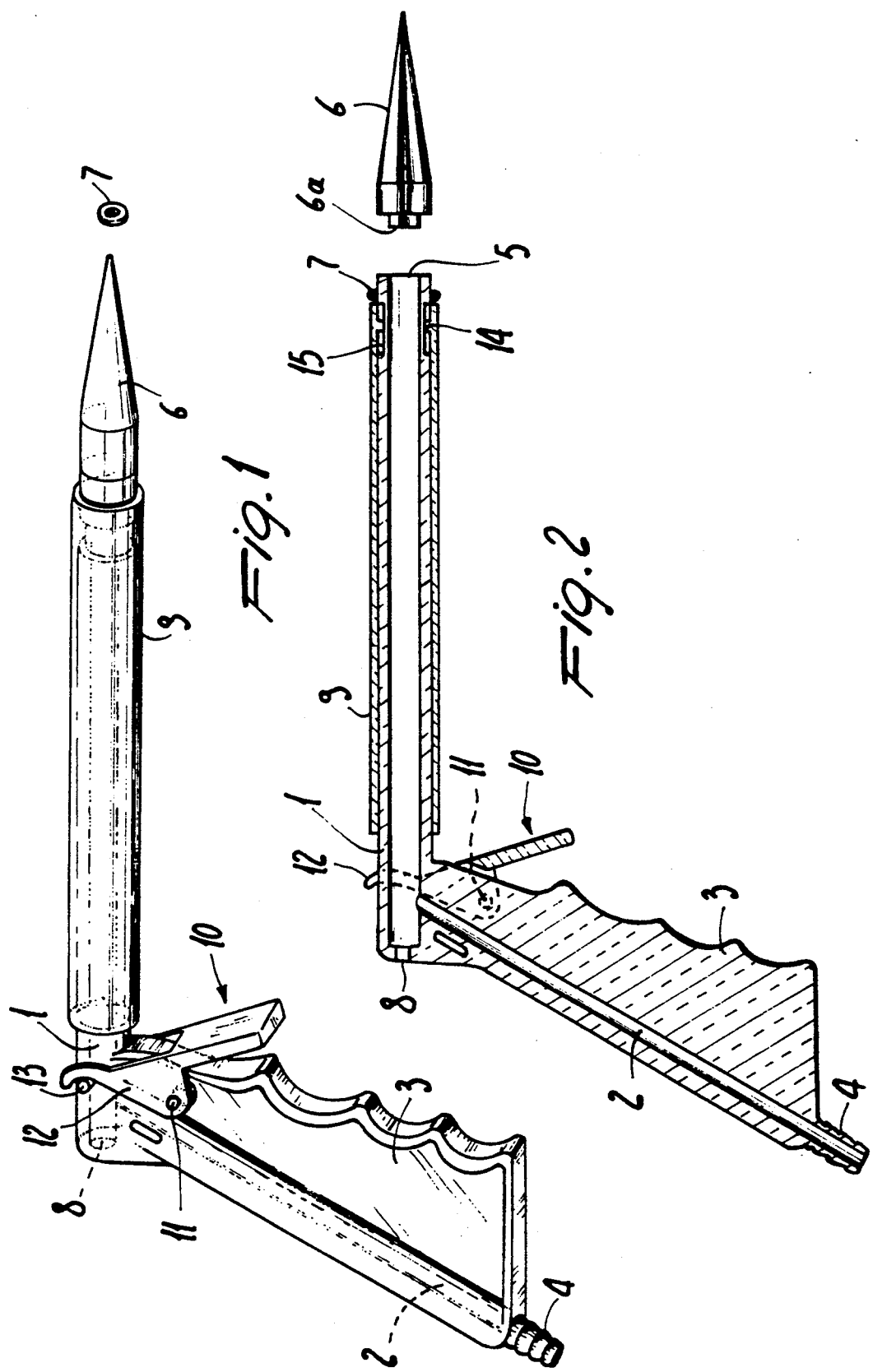

INSTRUMENT FOR THE LIGATION OF HEMORRHOIDS OR THE LIKE

BACKGROUND OF THE INVENTION

The present invention relates to an instrument for the ligation of hemorrhoids or the like.

Various methods for the therapy of hemorrhoids are currently used when said hemorrhoids no longer respond to strictly medical cures or when their size becomes such that any non-surgical therapy would produce no result or even negative results.

A first method is the strictly surgical one, which is irreplaceable in case of considerable internal and external prolapses.

This is a painful method which entails significant postoperative hospitalization and is also usually rather destructive as regards the muscles of the anal-proctorectal tract.

A second method is constituted by cryosurgery, which in practice consists in "freezing" the hemorrhoids at temperatures which can vary between −59 degrees Celsius and −89 degrees Celsius for cycles lasting a few minutes.

Another method is constituted by thermosurgery, which uses devices which emit flows of heat at preset temperatures and for limited periods of time.

A method which is currently having considerable success, since it is the easiest, quickest and most practical, as well as the least painful and least damaging, is the so-called "throttling" surgery.

This method consists in applying an elastic ring of adequate size on the "neck" of the hemorrhoid, leaving it in place until the hemorrhoid necrotizes and falls away spontaneously due to the occlusion of the blood supply pathways.

The time required in order to achieve this effect is relatively short, the results are extremely positive and the method, which is typically ambulatory, is not painful.

A cylindrical bush is used to apply the ligature to the "neck" of the hemorrhoid, and the elastic ring is arranged around said bush, dilating the ring considerably, by means of a conical applicator.

Once the hemorrhoid has been passed through said bush, the elastic ring is caused to slide, moving it so that it surrounds the "neck" of the hemorrhoid and, by pressing on it, performs the throttling action.

Two methods are currently used to make the hemorrhoids pass in the bush.

A first one of said methods consists in making a special instrument pass through the bush; said instrument is provided with a forceps at its end, which is suitable for gripping a portion of the hemorrhoid and for pulling it inside the bush.

This method has a series of problems, some of which are considerable; first of all, the need arises to use both hands, one for the bush and one for the instrument provided with the forceps.

It is furthermore rather traumatic, since the forceps can break the wall of the hemorrhoid.

Furthermore, it is not always possible to achieve the passage of the entire mass to be throttled.

In a second method, which is pneumatic, the bush constitutes the end of a duct which is connected to an aspirator which, when actuated, aspirates the hemorrhoid inside said bush.

Although this method has the advantage that it does not break the wall of the hemorrhoid and can be performed with one hand, it has the problem that during the operation the bush is constantly at negative pressure, so that the hemorrhoid cannot be disengaged in case of incorrect grip; furthermore, at the end of the operation it is necessary to disconnect the aspiration system from the instrument in order to be able to disengage the hemorrhoid.

For both "throttling" methods, the typically metallic material of which the instruments are made must be resterilized after each use and, since such materials are not transparent, it forces the operator to work practically blind.

The instruments themselves are furthermore considerably expensive.

SUMMARY OF THE INVENTION

The aim of the present invention is to provide a new instrument for applying the method for curing hemorrhoids or the like by "throttling" which solves or at least reduces the problems described above in the known art.

Within the scope of the above aim, a consequent primary object is to provide an instrument which allows to disengage a hemorrhoid or the like in case of incorrect grip and to engage it again rapidly and without problems.

Another important object is to provide an instrument which is suitable even for considerable hemorrhoidal volumes.

Another important object is to provide an instrument by means of which operations can be monitored visually.

Yet another object is to provide a disposable instrument which can thus be supplied in pre-sterilized form so as to prevent cross-infections and contagions.

Still another object is to provide an instrument characterized by extreme ease of use.

Yet another object is to provide an instrument which can be manufactured in large series and at low cost, so that it can be marketed at an extremely competitive price.

This aim, these objects and others which will become apparent hereinafter are achieved by an instrument for the ligation of hemorrhoids or the like, which comprises a substantially cylindrical container with a coupling for connection to an air aspiration apparatus and a grip handle for the operator, said container being suitable for internally accommodating a hemorrhoid or the like aspirated through its open end, on which a dilated ring-like elastic ligature, to be transferred so as to throttle the "neck" of the hemorrhoid or the like, is arranged circumferentially and externally, said instrument being characterized in that said container is provided with means suitable for adjusting the pressure inside it while the aspiration apparatus is operating.

BRIEF DESCRIPTION OF THE DRAWINGS

Further characteristics and advantages of the invention will become apparent from the detailed description of an embodiment thereof, illustrated only by way of non-limitative example in the accompanying drawings, wherein:

FIG. 1 is a lateral perspective view of the instrument according to the invention;

FIG. 2 is a longitudinal sectional view of the instrument of FIG. 1.

DESCRIPTION OF THE PREFERRED EMBODIMENTS

With reference to the above figures, the instrument for the ligation of hemorrhoids or the like, completely made of transparent or partially transparent plastic material, for example by injection-molding, comprises an elongated cylindrical container 1 having an internal passage; a coupling duct 2 for connection to an air aspiration apparatus, not illustrated, ends at a region which is adjacent to the bottom of said container and is in communication with the passage thereof.

Said coupling 2 extends externally, in a first handle portion 3, which gives the assembly the appearance of a sort of pistol, in which a user's palm can be wrapped around the handle position.

In a second terminal portion, said coupling 2 is provided with external annular ridges 4 for the coupling of the hose for connection to said aspiration apparatus.

Said container 1 is suitable for accommodating, inside its open end 5, a hemorrhoid or the like aspirated by the previously mentioned apparatus.

A ring-shaped elastic ligature 7 is conveniently arranged circumferentially on the outside of said end 5, by means of a funnel-shaped conical applicator 6 which is provided with a tang 6a which removably couples to said end 5.

As can be seen in the figures, said ligature 7 is extremely dilated with respect to its inactive condition when it is arranged on the end 5.

According to the invention, the bottom of said container 1 is provided with a hole 8 which allows manual adjustment of the pressure inside the container 1.

In practice, said hole 8 is arranged so that it can be very easily closed by the thumb of the hand that grips the instrument, so that while the aspiration apparatus is operating, negative-pressure or atmospheric-pressure conditions are obtainable inside said container 1.

A tubular pusher element 9 is slidingly externally coupled to said container 1 and extends between the region of the end 5 on which the ligature 7 is arranged and the coupling region of said handle 3, where a first-class lever element 10 is articulated to the instrument and is suitable for pushing the tubular pusher element 9 so that it disengages the ligature 7 from the end 5.

As can be seen from the figures, the lever element 10 is substantially shaped like a trigger, with articulation pivots 11 arranged laterally to the handle 3 and two fork-like wings 12 arranged between the edge of the element and corresponding stop pins 13 which are lateral to the bottom of the container 1.

Conveniently, said pusher element 9 is provided with an internal annular ridge 14 which is accommodated in a corresponding external annular groove 15 defined externally on the container 1.

This is provided in order to limit the sliding movements of the tubular element 9 to the extent strictly necessary.

The ridge 14 in any case has such a height as to allow it to pass beyond the obstacle constituted by the end 5 by deforming elastically when the element 9 is fitted to the container 1.

As regards the use of the instrument, after the ligature 7 has been positioned by means of the conical element 6 and after such conical element has been removed, the aspiration apparatus is started and the handle 3 is gripped, closing the hole 8 with the thumb.

At this stage the end 5 can be positioned at the hemorrhoid or the like, which is aspirated inside the container 1.

The operation is performed in viewing conditions, since the instrument, as mentioned previously, is made of transparent material.

It is thus possible to see whether the hemorrhoid or the like has entirely entered the container 1 and thus press on the lever element 10 which, by moving the pusher element 9, transfers the ligature 7 around the "neck" of the hemorrhoid, throttling it.

If the hemorrhoid has been gripped incorrectly, the aspiration effect can be eliminated, returning the container to atmospheric pressure, by simply removing the thumb of the hand from the hole 8, thus opening it.

At this point it should be stressed that the diameter of the container 1 is considerable and is thus suitable for containing large hemorrhoidal volumes.

Furthermore, since the instrument is made of plastic material, it is disposable and also has an extremely modest cost.

The fact that the instrument can be operated with one hand and without having to disconnect the aspiration apparatus during the operation is also highly significant.

In practice it has thus been observed that the instrument according to the invention has achieved the intended aim and objects of the present invention.

The invention thus conceived is susceptible to numerous modifications and variations, all of which are within the scope of the inventive concept.

Thus, the handle 3 and the container 1 may be non-monolithic and may be mutually interchangeably associated, for example with a snap-together coupling In this manner, the handle may be made of a non-disposable material, for example stainless steel, whereas the part which relates to the container 1 and to the pusher element 9, made of plastic material, can be changed at each operation.

Furthermore, all the details may be replaced with other technically equivalent elements; thus, for example, the tubular pusher element may be replaced with pusher elements having another shape which can in any case slide on the outside of the container 1.

In practice, the materials employed, so long as compatible with the contingent use, as well as the dimensions, may be any according to the requirements.

I claim:

1. Ligation instrument, particularly for hemorrhoids, comprising:
    a substantially cylindrical container having an open end about which an elastic dilated ligature element is circumferentially and externally positionable, and a passage extending inside said container from said open end;
    a grip handle for an operator's palm to which is rigidly connected said cylindrical container in such a manner that said grip handle and said cylindrical container form a pistol-like assembly;
    a coupling duct which extends inside said handle portion and which is in communication at a first end thereof with said passage of said cylindrical container, said coupling duct having a second end to which is connectable an air aspirator means;
    an aspiration hole which is in communication with said passage of said cylindrical container and which is arranged so as to be easily blocked by a user's thumb during use;

pusher element means slidably arranged on said cylindrical container for engaging and pushing said dilated ligature element off said open end of said cylindrical container; and trigger lever means pivotally connected to said grip handle and actuatable by a user's fingers during use for actuating said pusher element means.

2. Ligation instrument according to claim 1, wherein said pusher element means comprises a tubular pusher element which is slidably guided around said cylindrical container by means of an internal annular ridge which is provided inside said tubular pusher element and which is slidably accommodated in an external annular groove provided on said cylindrical container, said tubular pusher element having a first end which is engageable by said trigger lever means and a second end which can engage and push said dilated ligature element off said open end of said cylindrical container.

3. Ligation instrument according to claim 2, wherein at least said tubular pusher element and said cylindrical container are made of plastic material, and wherein said cylindrical container is interchangeably fixed onto said grip handle.

4. Ligation instrument according to claim 2, wherein at least said second end of said tubular pusher element and said open end of said cylindrical container are transparent.

5. Ligation instrument according to claim 1, further comprising a conical applicator element which is connectable to said open end of said cylindrical container for applying said ligature element thereto.

6. Ligation instrument according to claim 1, wherein said pusher element means comprises a tubular pusher element which is slidably guided around said cylindrical container, said tubular pusher element having a first end which is engageable by said trigger lever means and a second end which can engage a push said dilated ligature element off said open end of said cylindrical container, and wherein said trigger lever mean comprise a lever element which is pivotally connected to said grip handle which comprises an upwardly protruding pair of fork wings arranged about said cylindrical container for engaging said first end of said pusher element.

* * * * *